US006107805A

United States Patent [19]
Abdel-Rahman

[11] Patent Number: 6,107,805
[45] Date of Patent: Aug. 22, 2000

[54] EXTENDED DETECTION ZONE IN AN IONIZATION DETECTOR

[75] Inventor: Mahmoud F. Abdel-Rahman, West Grove, Pa.

[73] Assignee: Agilent Technologies, Inc., Santa Clara, Calif.

[21] Appl. No.: 09/070,003

[22] Filed: Apr. 30, 1998

[51] Int. Cl.[7] .......................... G01N 27/62; G01N 37/00; G01T 1/18

[52] U.S. Cl. .......................... 324/464; 324/459; 324/469; 324/468; 250/384; 73/28.02

[58] Field of Search ................................... 324/464, 459; 250/384; 73/28.02

[56] References Cited

U.S. PATENT DOCUMENTS

| | | |
|---|---|---|
| 4,789,783 | 12/1988 | Cook . |
| 4,975,648 | 12/1990 | Lawson et al. . |
| 5,153,519 | 10/1992 | Wentworth et al. . |
| 5,317,271 | 5/1994 | Wentworth et al. ..................... 324/464 |
| 5,394,090 | 2/1995 | Wentworth et al. . |
| 5,394,091 | 2/1995 | Wentworth et al. ..................... 324/464 |
| 5,394,092 | 2/1995 | Wentworth et al. . |
| 5,528,150 | 6/1996 | Stearns et al. . |
| 5,532,599 | 7/1996 | Stearns et al. . |
| 5,541,519 | 7/1996 | Stearns et al. . |
| 5,594,346 | 1/1997 | Stearns et al. . |
| 5,920,072 | 7/1999 | Abdel-Rahman ....................... 250/384 |

OTHER PUBLICATIONS

G. Gremaud, W. E. Wentworth, A. Zlatkis, R. Swatloski, E.C.M. Chen, S. Stearns, "Windowless Pulsed–Discharge Photoionization Detector Application To Qualitative Analysis Of Volatile Organic Compounds", accepted Aug. 18, 1995, Journal of Chromatography A. 724 (1996) pp. 235–250.

Herbert H. Hill and Dennis G. McMinn, Dept. of Chemistry, Washington State University, Pullman, Washington; "Detectors for Capillary Chromatography"; Chemical Analysis Series, vol. 121; ISBN 0–471–50645–1; 1992 John Wiley & Sons, Inc.

Primary Examiner—Glenn W. Brown
Assistant Examiner—James C Kerveros

[57] ABSTRACT

An ionization detector for detection of an analyte includes a source chamber having a source of ionizing particles and receiving a fluid stream of detector gas; an ionization chamber connected to the source chamber at an ionization chamber entrance therebetween so as to allow metastables and photons to be generated in the source chamber and to be transferred in the fluid stream to the ionization chamber; a signal electrode assembly located in the ionization chamber; and a signal measuring circuit for measuring ionized analyte molecules. The signal electrode assembly includes a spaced array of electrodes including a collector electrode, a first signal electrode, and a second signal electrode. The first signal electrode is situated immediately downstream from the ionization chamber entrance and substantially upstream of the collector electrode, so as to extend the detection zone to the vicinity of the ionization chamber entrance.

7 Claims, 6 Drawing Sheets

EXTENDED DETECTION ZONE IN AN IONIZATION DETECTOR

FIELD OF THE INVENTION

This invention relates generally to detectors for analysis of a sample gas; and more particularly, to an ionization detector having an extended detection zone for more efficient detection of analytes.

BACKGROUND OF THE INVENTION

As illustrated in FIG. 1, an ionization detector 100 typically comprises a body 102 having a first chamber 110 for generation of ionizing particles and a second chamber 120 connected to the first chamber 110 for receiving a sample gas 122. The sample gas 122 is conveyed in a carrier gas and is provided to the second chamber 120 by a conduit 130 which typically is provided in the form of a separation column. The first chamber 110 includes a source of ionizing particles (not shown), such as a radioactive source or an electrical discharge, and is typically swept by a detector gas 112 selected from the class of known noble gases. The presence of the detector gas 112 in the first chamber 110 causes ionizing particles, in the form of photons and metastables, to be produced. The flow of the detector gas 112 from the first chamber 110 to the second chamber 120 causes the ionized particles to be mixed with the sample gas 122, thus causing the sample molecules of interest, considered herein as analytes, to be ionized. The second chamber 120 includes electrodes 124,126,128 for detecting the ionized sample molecules by use of an electrometer circuit (not shown) connected to the electrodes 124,126, 128.

Detector sensitivity may be measured in a plot of detector response versus analyte concentration or analyte quantity. The range over which the detector sensitivity is constant is called the linear dynamic range, and the entire range over which the response is variable with analyte concentration or quantity is called the dynamic range of the detector. The upper limit of the dynamic range is determined when detector sensitivity falls to an unusable value, typically zero, and the detector is said to be saturated. The lower limit of the dynamic range occurs at a minimum detectable level (MDL).

Particular examples of ionization detectors include the electron capture detector and the discharge ionization detector.

Electron capture detectors for gas chromatography are well known in the art. This type of detector offers high sensitivity and high selectivity towards electrophilic compounds and is widely used for detecting trace amounts of pesticides in biological systems and in food products. Such compounds typically contain halogens which combine with free electrons that are created in the ionization chamber in the detector. The resulting decrease in free electrons in the ionization cell is monitored as an indication of the concentration of the compounds in a sample.

A discharge ionization detector operates by applying a high voltage across discharge electrodes that are located in a gas-filled source chamber. In the presence of a detector gas such as helium, a characteristic discharge emission of photons occurs. The photons irradiate an ionization chamber receiving a sample gas that contains an analyte of interest. Ions are produced in the ionization chamber as a result of photon interaction with ionizable molecules in the sample gas. Helium metastables are also generated in the source chamber and are found to play a role in ionization of the analyte of interest.

FIG. 2 illustrates a linearity plot 200 that is typical of the dynamic range of a helium discharge ionization detector. The magnitude of the ionized analyte molecules is manifested as a current that can be measured to ascertain the composition of one or more analytes. In the illustrated linearity plot, the analyte is carbon-12 ($C_{12}$). The response factor should ideally be constant (in other words, flat) irrespective of the amount of the analyte introduced into the detector. As illustrated, the response factor is flat over the linear dynamic range 210 but decreases in a second region 220 when higher amounts of analyte are introduced to the detector.

Although the design of ionization detectors continues to be an object of study in the prior art, there nonetheless exists a need for an ionization detector having a detector response that exhibits greater linear dynamic range.

SUMMARY OF THE INVENTION

The present invention is directed to an ionization detector having an improved dynamic range, lower minimum detectable level (MDL), and a greater signal-to-noise ratio in the detector response.

Detector response in an ionization detector is based on an accurate measurement of the ionized analyte of interest. More efficient generation of metastables and photons in a volume of noble gas will therefore improve certain characteristics of the detector response, such as the minimum detectable level (MDL), and signal-to-noise ratio.

I have found that conventional ionization detectors suffer from a loss of such metastables and photons when analyte molecules are allowed to diffuse away from a detection zone in an ionization chamber toward the source of ionization particles in a source chamber (such movement of analyte molecules is hereinafter described as analyte diffusion). Analyte diffusion allows the analyte molecules to combine with the ionizing particles at points located well upstream of the detection zone. As a result, fewer analyte molecules are detected in the detection zone and fewer ionizing particles can progress to the detection zone. When there is a high concentration of analyte molecules in the ionization chamber, the number of ionizing particles that reach the detection zone becomes significantly less, and the detector response is unstable or nonlinear.

As a result of my findings, I have discovered an opportunity to achieve improved dynamic range, lower minimum detectable level (MDL), and greater signal to noise ratio in the detector response by extending the detection zone, such that the combination of the extended detection zone will detect the presence of analyte molecules in a greater proportion of the volume of the ionization chamber. Preferably, the detection zone is extended to the entrance of the ionization chamber, and hence is most proximate the source chamber, so as to allow detection of analyte molecules that diffuse toward the source chamber. Otherwise, the analyte molecules would be subject to diffusion but not detection. As a result, the natural movement of analyte molecules will occur largely within the extended detection zone such that they continue to be subject to detection.

Accordingly, the present invention is directed to an ionization detector having a detector body that defines an ionization chamber and an adjacent source chamber, and a novel signal electrode assembly situated in the ionization chamber so as to create an extended detection zone in the ionization chamber.

Preferably, the invention contemplates the use of a source chamber having a source of ionizing particles and receiving a fluid stream of detector gas (preferable selected from a group of noble gases, and most preferably being helium or argon). The detector gas stream flows through the source chamber and into the ionization chamber so as to allow metastables and photons to be generated in the source chamber and to be immediately transferred to the detection zone. In addition, the signal electrode assembly is connected to a signal measuring circuit whereby the ionized analyte molecules may be subject to measurement with use of an electrometer. As a result, analyte diffusion from the ionization chamber toward the source chamber, which heretofore would escape the conventional detection zone, is now subject to detection in the extended detection zone.

The signal electrode assembly includes a spaced array of electrodes including a collector electrode, a first signal electrode, and a second signal electrode. The first signal electrode in the signal electrode assembly is situated well upstream of the collector electrode so as to extend the detection zone. Furthermore, the collector electrode repels negative ions that originate in the source chamber so as to prevent them from entering the detection zone. The collector electrode also collects positive ions. The collector electrode thus reduces the passage of ions into the detection zone, the presence of which would otherwise reduce the sensitivity of the detector. The collector electrode allows photons and metastable to pass freely from the source chamber to the detection zone.

In a feature of the present invention, and in a departure from the prior art, the first signal electrode is located adjacent to, and immediately downstream from, an entrance that defines the transition between the source chamber and the ionization chamber. A secondary portion of the detection zone is effected between the second signal electrode and the collector electrode, and a primary portion of the detection zone is effected between the collector electrode and the first signal electrode. The spaced array of electrodes thereby cause a greater volume within the ionization chamber to be subject to detection in comparison to the volume defined by the detection zone in a conventional ionization detector. Preferably, the extended detection zone occupies the majority of the volume of the upstream end of the ionization chamber.

In another preferred embodiment of the invention, the source chamber includes an ionizing particle source provided in the form of a discharge electrode assembly having first and second discharge electrodes located so as to enable the creation of a discharge in the source chamber in close proximity to the ionization chamber entrance located between the source chamber and the ionization chamber. In this preferred embodiment, the first and second discharge cathodes are located upstream of the ionization chamber entrance between the source chamber and the ionization chamber. Preferably, the first discharge electrode is located upstream of the second discharge electrode. The discharge is thereby preferentially created between the first and second discharge electrodes and is unlikely to occur between either of the first or second discharge electrodes and the first signal electrode. Metastables and photons generated in the discharge are rapidly and effectively swept by the flow of the detector gas into the ionization chamber for ionization of analytes in the column effluent.

In another preferred embodiment of the invention, the source chamber includes an ionizing particle source provided in the form of a radioactive material which is situated in at least one side wall of the source chamber. The ionizing particle source is located so as to enable the creation of a plurality of ionizing particles in close proximity to the ionization chamber entrance.

BRIEF DESCRIPTION OF THE DRAWINGS

The foregoing and other features and advantages of the invention will be apparent from the following more particular description of preferred embodiments of the drawings, in which like reference characters refer to the same parts throughout the different views. The drawings are not necessarily to scale, emphasis instead being placed upon illustrating the principles of the invention.

DETAILED DESCRIPTION OF THE PREFERRED EMBODIMENTS

The apparatus and methods of the present invention may be employed in particular to improve the detection of an analyte that may be present in a variety of fluids. Gases are the preferred fluids according to the practice of the present invention, and therefore the following description of the invention will include a description of the arrangement, construction, and operation of a novel discharge ionization detector for use in a gas sample analytical system. The teachings of this invention apply to any detector operating on the principle of ionization of a fluid mixture, and as such include a helium ionization detector, argon ionization detector, and other detectors such as electron capture detectors having either radioactive or non-radioactive electron sources. One particular application of the novel discharge ionization detector is in a chromatographic analytical system (hereinafter, a chromatography however, other applications such as process sampling systems, gas leak detection systems, air quality monitoring systems, and the like are contemplated.

For the purposes of the description herein, certain terms are defined as follows:

A detector gas may be considered to include a gas selected for the purpose of generating ionizing particles in a source chamber, and is preferably selected from the class of gases known as the noble gases. The preferred detector gas may include a mixture of one or more noble gases. A preferred noble gas is helium.

A source of ionizing particles may be considered to include an electrical discharge source, a photo-ionization source, or a radioactive source.

Ionizing particles may be considered to include photons and metastables.

The quality of being "extended", in reference to a detection zone refers to a detection zone of substantially greater proximity to the ionizing particle source than is known for a typical detection zone in ionization detectors of the prior art, and in particular to a detection zone that is extended to the ionization chamber entrance, so as to be immediately adjacent the transition between the source chamber and the ionization chamber.

Figure 1:
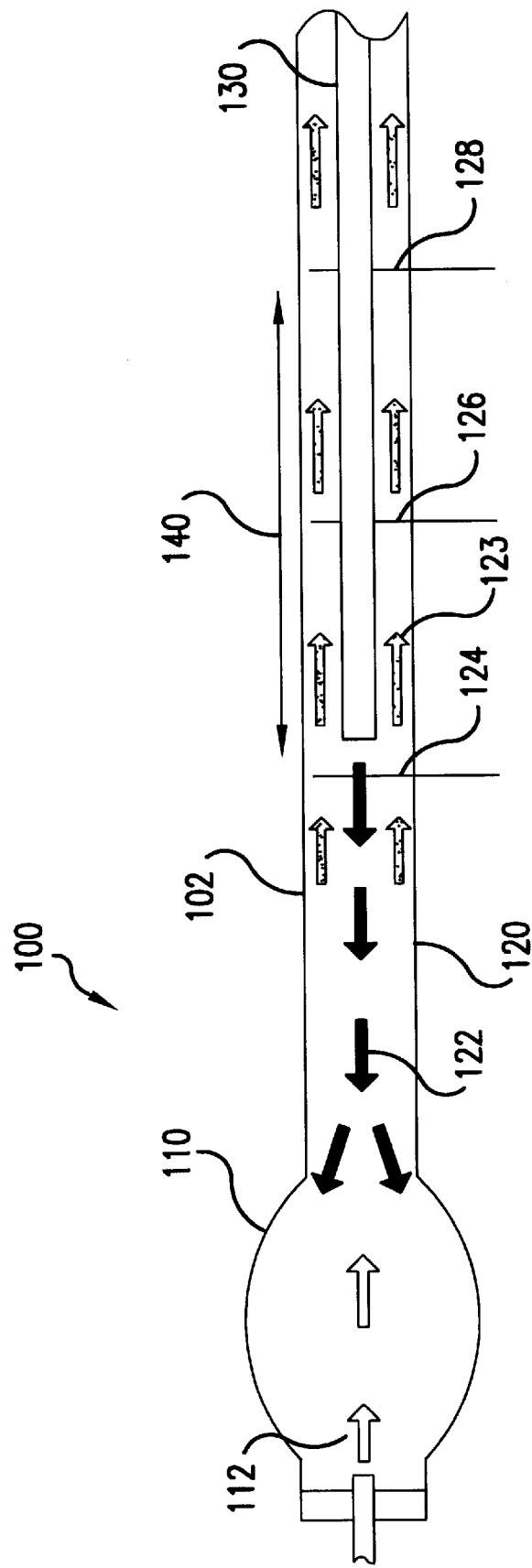
FIG. 1 is a simplified schematic view of a conventional ionization detector constructed according to the prior art.
Figure 2:
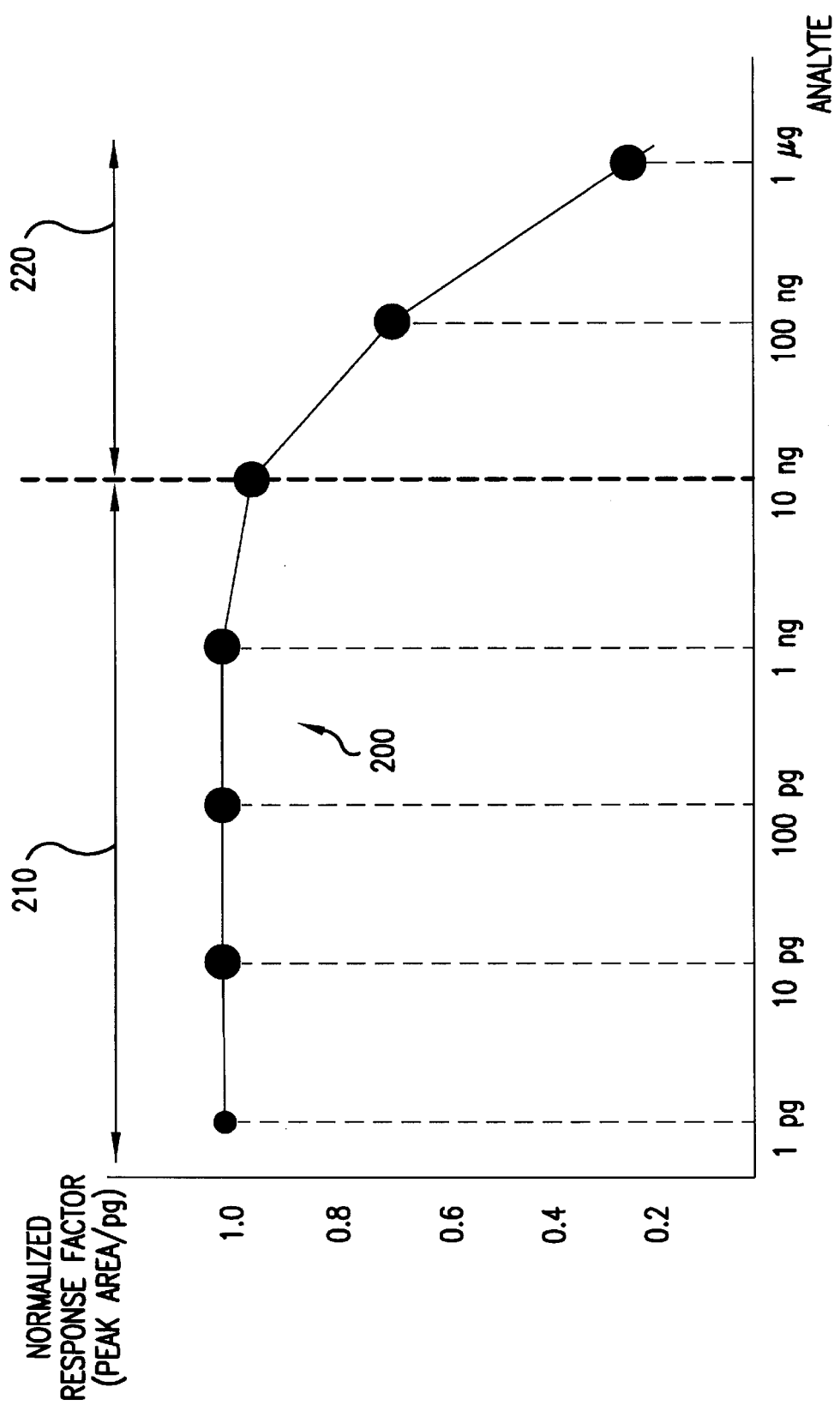
FIG. 2 is a graphical representation of the normalized response factor exhibited by a conventional ionization detector of the prior art.
Figure 3:
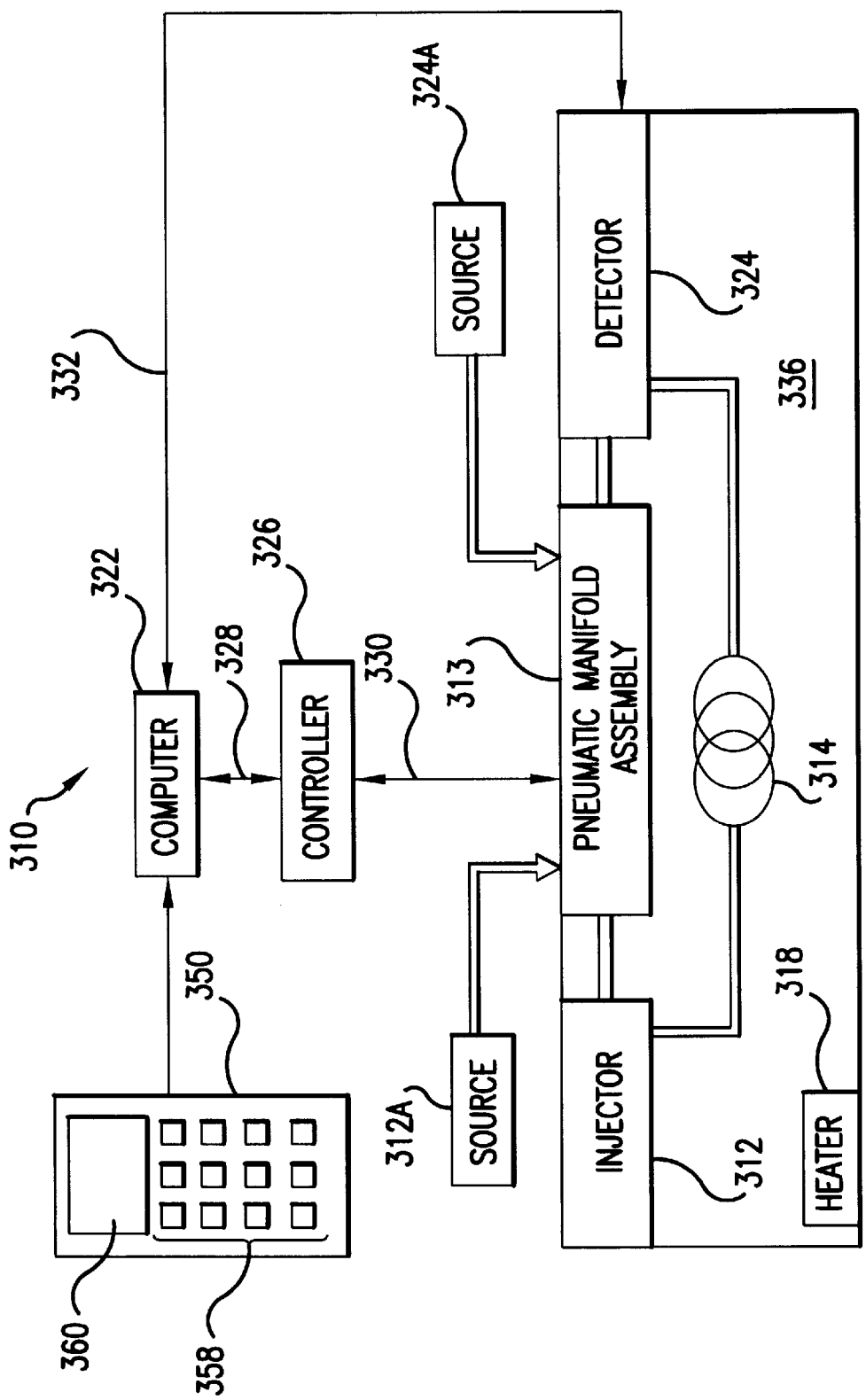
FIG. 3 is a simplified schematic representation of an analytical instrument having therein an improved ionization detector constructed according to the present invention.

Accordingly, a novel ionization detector may be designed for use in an analytical instrument as shown in FIG. 3. The instrument is generally designated chromatograph 310. In the preferred embodiment, the chromatograph 310 is a Hewlett-Packard HP6890 gas chromatograph that is modified to include a novel ionization detector 400 constructed according to the teachings herein.

Operation of the chromatograph 310 may be generally understood as follows. In order to perform a chromatographic separation of a given sample compound, a sample is injected with a pressurized carrier gas by means of an injector 312. The carrier gas supplied to injector 312 is provided from a source 312A through one or more pneumatic manifold assemblies 313, each of which serves in part to control and redirect a plurality of gas flows, including the carrier gas and one or more detector gas of appropriate types. The detector gas are provided from respective sources (one such source 324A is shown) to the pneumatic manifold assembly 313. Suitable fluid-handling devices such as valves, sensors and the like in the pneumatic manifold assembly 313 are operated under the control of the computer 322 and controller 326 by way of control signals provided on a data and control lines 328, 330, 332. The control and data line 330 also allows the return of sense information from suitable sensors and signal-interface electronics that are provided in the pneumatic manifold assembly 313. Another set of data and control lines 332 allows the transfer of detector output signal information between the detector 400 and the computer 322.

A separation column 314 is positioned within an oven 336. The carrier gas/sample combination passing through column 314 is exposed to a temperature profile resulting in part from the operation of a heater 318 within oven 336. During this profile of changing temperatures, the sample will separate into its components primarily due to differences in the interaction of each component with the column 314 at a given temperature. As the components exit column 314 they are detected by the detector 400.

Computer 322 maintains overall control of the systems associated with chromatograph 310. It will be recognized that any particular gas chromatograph may include more systems than those described in relation to the present invention. For example, an electronic control panel 350 is shown to include an operator interface provided in the form of a keypad 358 and a display 360. It will also be understood that although computer 322 is shown as a single block, other embodiments are contemplated; for example, the functions of the computer 322 may be subsumed into one unit. The computer 322 includes a central processing unit and all associated peripheral devices, such as random access memories, read-only memories, input/output isolation devices, clocks, and, preferably, a digital signal processing unit, and other related electronic components. In the preferred embodiment, the central processor used in computer 322 is a microprocessor.

Figure 4:
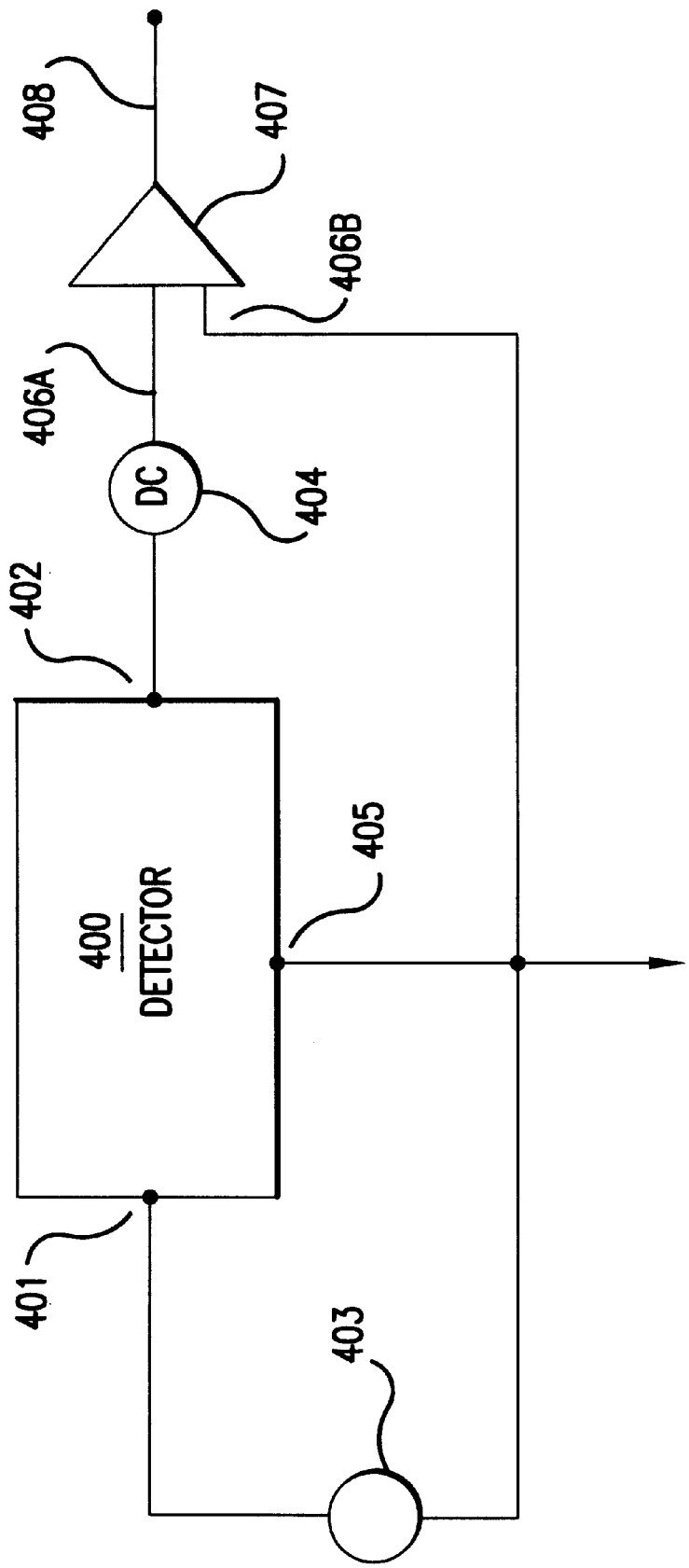
FIG. 4 is a schematic of the ionization detector of FIG. 3.

As illustrated in FIG. 4, a preferred embodiment of the ionization detector 400 of FIG. 3 may be constructed according to the invention as having a discharge cathode connector 401 connected in series to a discharge voltage supply 403. (Alternatively, the preferred embodiment of detector 400 may be constructed according to the invention to include a radioactive source material in lieu of a discharge source for provision of ionizing particles, and accordingly the discharge cathode connector 401 and the discharge voltage supply 403 may be omitted.) The detector 400 further includes a signal cathode connector 402, a signal bias voltage supply 404, and a common connector 405 (which is connected to a ground potential). Differential inputs 406A, 406B in an electrometer 407 may be connected to the signal bias voltage supply 404 and the common connector 405 so as to provide a detector output signal on a detector output signal line 408 for measuring the current passing between the signal cathode connector 402 and the common connector 405.

Figure 5:
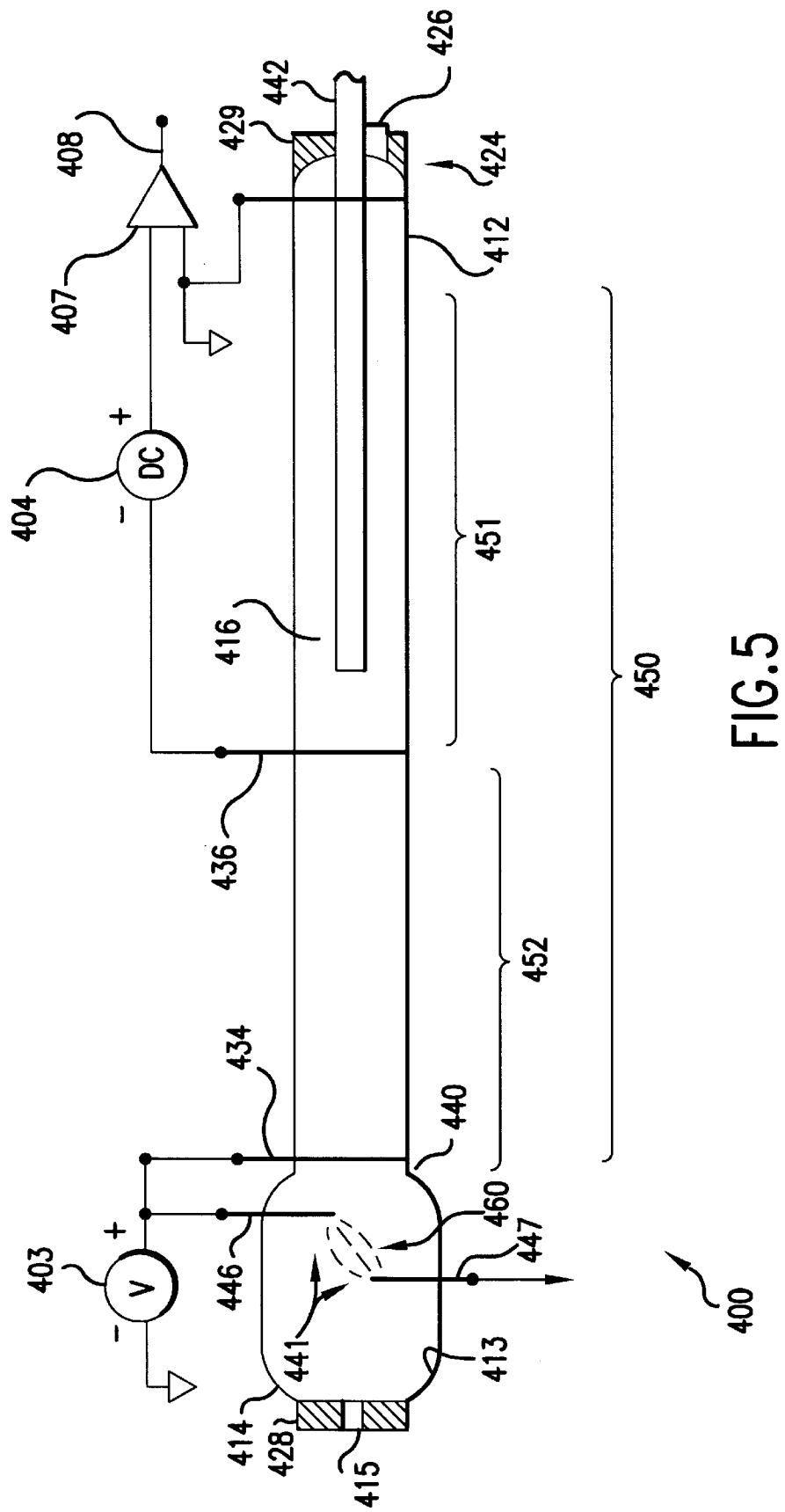
FIG. 5 is a simplified diagrammatic representation of the discharge ionization detector of FIG. 3.

As illustrated in greater detail in FIG. 5, the detector 400 is constructed to include a detector body 412 defining first and second adjacent chambers, preferably constructed as source chamber 414 and ionization chamber 416, respectively, which are joined at an ionization chamber entrance 440 by a common internal wall 418. The detector body 412 is preferably provided in the shape of a tubular member. The source chamber 414 includes a source of ionizing particles such as a discharge electrode assembly 441 having discharge electrodes 446, 447 for provision of ionizing particles from an electrical discharge 460. (Alternatively, a radioactive material may be provided as a source of ionizing particles in a side wall 413 of the source chamber 414, in lieu of the discharge electrode assembly 441, as may be selected and constructed by those skilled in the art.)

The body 412 includes an inlet 415 to the source chamber 414 for admitting a controlled fluid stream of detector gas, preferably one of the noble gases such as helium. An inlet 424 to the ionization chamber 416 includes a column receiving structure 429 for receiving a conduit 442. Preferably, the conduit 442 is provided in the form of a conventional separation column for admitting a sample gas having an analyte therein to be detected. The body 412 of the detector 400 is preferably constructed of a two-part, generally elongate configuration, with the source chamber 414 being the first part and the ionization chamber 416 being integrated in the second part. The volume of the ionization chamber 416 is preferably in the range of 10 to 100 microliters and in some applications may be less than 2 microliters and as large as 1,000 milliliters. In the illustrated embodiment, the detector body 412 is preferably of unitary construction having the discharge and ionization chambers 414, 416 provided in an electrically insulating and chemically inert material such as quartz, high-purity ceramic material, or silica according to known construction techniques. The detector gas inlet 415, sample gas inlet 424, and vent outlet 426 may suitably be constructed to include passageways extending through the appropriate fittings 428, 429 on the detector body 412.

The general direction of the detector gas flow proceeds from the source chamber 414 through the ionization chamber 416 to the vent 426, and such direction of gas flow will be considered herein as being "downstream". An extended detection zone 450 is effected by a signal electrode assembly that preferably includes a collector electrode 436 and first and second signal electrodes 434,438. The signal electrode assembly is connected, by way of the illustrated electrical connections, to polarizing voltage sources 403, 404 and an electrometer 407. The output of the electrometer 407 may be connected to appropriate means known in the art, so as to record or display an indication of the amount of ionized analyte components present in the detection zone 450. The first signal electrode 434 is preferably connected to a bias voltage so as to cause analyte ions to be collected by the collector electrode 436 while repelling ions that originate in the source chamber 414.

The polarizing voltage on the signal electrode assembly creates an electric field within the interior wall 418 of the ionization chamber 416 so as to define an extended detection zone 450. A secondary detection zone 451 is created between the second signal electrode 438 and the collector electrode 436, and a primary detection zone 452 is created between the first signal electrode 434 and the collector electrode 436.

In the illustrated embodiment, the electrodes 434, 436, 438 are disposed within the ionization chamber 416 so as to be aligned with the major central axis of the detector body 412. The first signal electrobe 434 is disposed in close proximity to, and in substantially parallel alignment with, the ionization chamber entrance 440. Accordingly, the secondary detection zone 451 is approximately commensurate with the size of a typical detection zone in a conventional ionization detector, and the primary detection zone 452 occupies a volume within the ionization chamber 416 that heretofore was not subject to detection. The combination of the secondary and primary detection zones 451, 452 thereby provides an extended detection zone 450 that occupies the majority of the ionization chamber 416, thus enabling improved detection of analyte molecules including those analyte molecules which may be subject to analyte diffusion.

Figure 6:
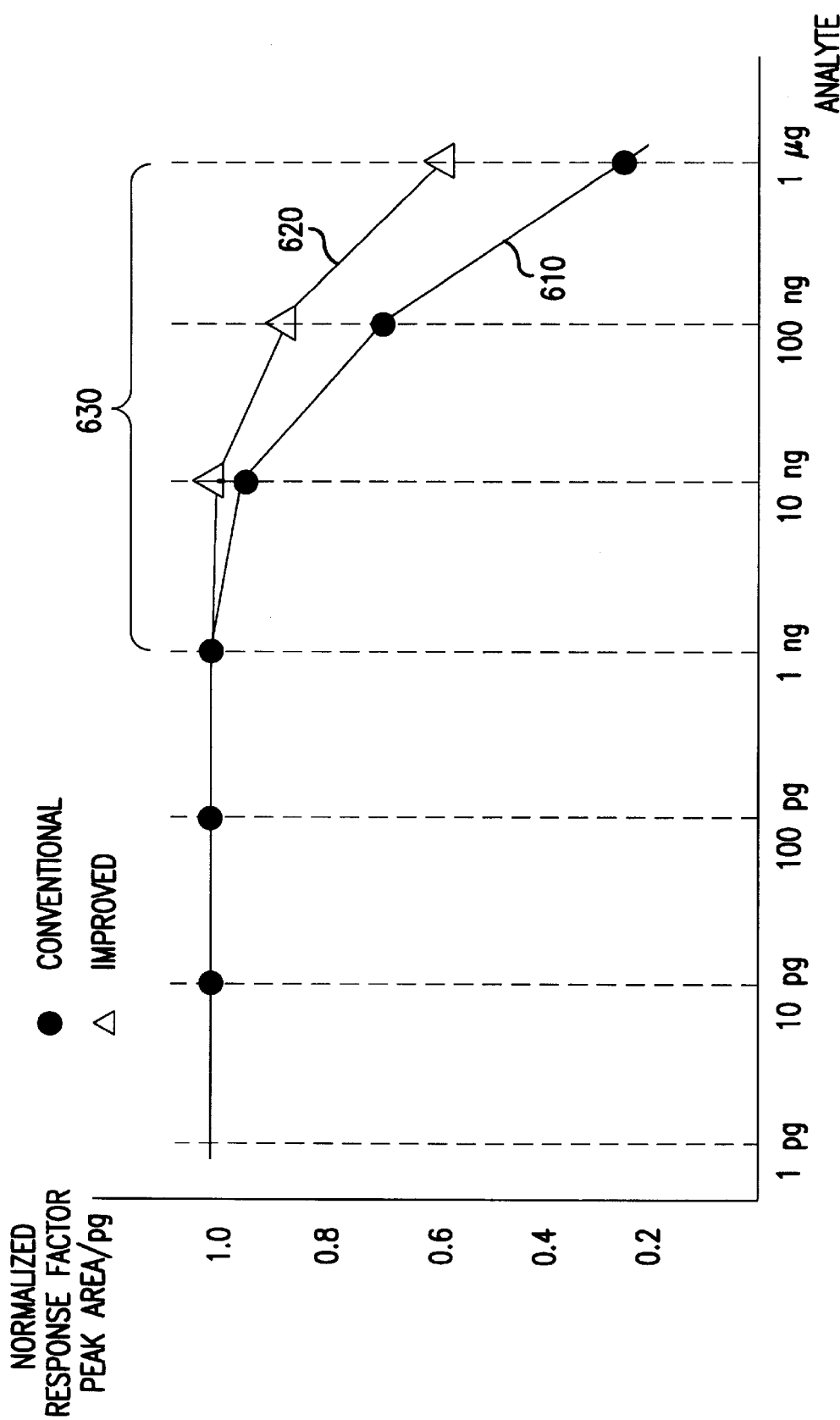
FIG. 6 is a graphical representation of a conventional normalized response factor exhibited by a discharge ionization detector constructed according to the prior art and an improved normalized response factor exhibited by an ionization detector constructed according to the present invention.

FIG. 6 illustrates a first plot 610 of the normalized response factor of a discharge ionization detector constructed according to the prior art, and a second plot 620 of the normalized response factor of a discharge ionization detector constructed according to the present invention. Both detectors received a sample of carbon-12. The plot 620 indicates an improved response factor that is flat in an extended response region 630 and is not subject to a significant reduction until an analyte amount greater than approximately 100 nanograms was introduced to the discharge ionization detector.

What is claimed is:

1. An apparatus for detecting an analyte, comprising:
   an ionization chamber having an opening through which analyte is supplied thereto and having an opening through which ionizing particles are supplied thereto for interaction with the analyte;
   a field electrode located at the opening through which ionizing particles are supplied;
   a collector electrode spaced apart from the field electrode;
   a voltage source connected to the field electrode, and
   a voltage source connected to the collector electrode, such voltage source for biasing the collector electrode to a negative voltage with respect to the field electrode, the voltage source connected to the field electrode for biasing the field electrode to a voltage that promotes the collection of ionized analyte by the collector electrode.

2. The apparatus of claim 1 wherein the opening through which analyte is supplied is the exit of a separation column.

3. An apparatus for detecting an analyte, comprising:
   an ionization chamber having an opening through which analyte is supplied thereto and having an opening through which ionizing particles are supplied thereto for interaction with the analyte;
   a field electrode located at the opening through which ionizing particles are supplied;
   a terminal electrode located within the ionization chamber and spaced apart from the field electrode;
   a collector electrode located between and spaced apart from the field and terminal electrodes, the collector electrode being at a voltage negative with respect to them, and
   a voltage source connected to the field electrode for biasing the field electrode to a voltage that promotes the collection of ionized analyte by the collector electrode.

4. The apparatus of claim 3 wherein the collector electrode and the terminal electrode are in electrical communication with a signal measuring circuit.

5. The apparatus of claim 3 wherein the opening through which analyte is supplied is located between the collector electrode and the terminal electrode.

6. The apparatus of claim 5 wherein the opening through which analyte is supplied is the exit of a separation column.

7. An apparatus for detecting an analyte, comprising:
   an ionization chamber having an opening through which analyte is supplied thereto and having an opening through which ionizing particles are supplied thereto for interaction with the analyte;
   a field electrode located at the opening through which ionizing particles are supplied;
   a terminal electrode located within the ionization chamber and spaced apart from the field electrode;
   a collector electrode located between and spaced apart from the field and terminal electrodes and being at a voltage negative with respect to them;
   a voltage source connected to the field electrode for biasing the field electrode to a voltage that promotes the collection of ionized analyte by the collector electrode;
   a signal measuring circuit in electrical communication with the collector electrode and the terminal electrode;
   a control system to direct the operation of the apparatus;
   wherein:
     the opening through which analyte is supplied is located between the collector electrode and the terminal electrode and is further comprised of a conduit in the form of separation column.

\* \* \* \* \*